US010961493B2

United States Patent
Higuchi et al.

(10) Patent No.: US 10,961,493 B2
(45) Date of Patent: Mar. 30, 2021

(54) CONTAINER FOR CELL ADMINISTRATION, STORAGE OR CULTURING

(71) Applicants: DAIKIN INDUSTRIES, LTD., Osaka (JP); OTSUKA PHARMACEUTICAL FACTORY, INC., Tokushima (JP)

(72) Inventors: Tatsuya Higuchi, Osaka (JP); Kozue Komazawa, Osaka (JP); Yoshiko Mohara, Osaka (JP); Takayuki Dempo, Tokushima (JP); Masuhiro Nishimura, Tokushima (JP)

(73) Assignees: DAIKIN INDUSTRIES, LTD., Osaka (JP); OTSUKA PHARMACEUTICAL FACTORY, INC., Tokushima (JP)

( * ) Notice: Subject to any disclaimer, the term of this patent is extended or adjusted under 35 U.S.C. 154(b) by 368 days.

(21) Appl. No.: 15/743,913

(22) PCT Filed: Jul. 14, 2016

(86) PCT No.: PCT/JP2016/003319
§ 371 (c)(1),
(2) Date: Jan. 11, 2018

(87) PCT Pub. No.: WO2017/010100
PCT Pub. Date: Jan. 19, 2017

(65) Prior Publication Data
US 2018/0201890 A1    Jul. 19, 2018

(30) Foreign Application Priority Data

Jul. 16, 2015 (JP) .............................. JP2015-142201
Jan. 13, 2016 (JP) .............................. JP2016-004339

(51) Int. Cl.
*C12M 1/00* (2006.01)
*A61K 35/28* (2015.01)
(Continued)

(52) U.S. Cl.
CPC ............. *C12M 23/20* (2013.01); *A61K 35/28* (2013.01); *C09D 127/18* (2013.01);
(Continued)

(58) Field of Classification Search
CPC ...... C12M 23/20; A61K 35/28; C09D 127/20; C09D 127/18; C09D 129/10; C12N 5/0663
See application file for complete search history.

(56) References Cited

U.S. PATENT DOCUMENTS

2007/0020754 A1*  1/2007  Yuge ..................... A61K 35/12
                                                                435/325
2007/0292945 A1   12/2007  Lin et al.
2012/0016089 A1*  1/2012  Takase ..................... C08F 8/00
                                                                525/326.2

FOREIGN PATENT DOCUMENTS

JP    H03-65177 A    3/1991
JP    H06-98756 A    4/1994
(Continued)

OTHER PUBLICATIONS

Henry et al. "A critical Review of the Application of Polymer of Low Concern and Regulatory Criteria to Fluoropolynners". Integrated Environmental Assessment and Management. vol. 14, No. 3, pp. 316-334. Feb. 9, 2018. (Year: 2018).*
(Continued)

*Primary Examiner* — Michael L Hobbs
(74) *Attorney, Agent, or Firm* — Greenblum & Bernstein, P.L.C.

(57) ABSTRACT

When mammal cells are administered by using a container whose surface in contact with the mammal cells is formed of a fluororesin material at least partially having a —$CF_3$ terminal group or a container whose surface in contact with the mammal cells is formed of a fluororesin material having a total number of non-fluorinated group terminals and
(Continued)

—CF$_2$H group terminals in the fluororesin of 70 or less per 1×10$^6$ carbon atoms, or mammal cells are stored or cultured in such a container, the cell adhesion on the container inner surface and the cell survival rate reduction can effectively be suppressed. Therefore, by using these containers, a mammal cell-containing liquid having a high concentration and a high proportion of living cells can be administered, stored or prepared, which contributes to regenerative medicine using the mammal cell-containing liquid (suspension liquid).

12 Claims, 1 Drawing Sheet

(51) Int. Cl.
  *C09D 127/18* (2006.01)
  *C09D 127/20* (2006.01)
  *C09D 129/10* (2006.01)
  *C12N 5/0775* (2010.01)

(52) U.S. Cl.
  CPC ......... *C09D 127/20* (2013.01); *C09D 129/10* (2013.01); *C12M 23/14* (2013.01); *C12N 5/0663* (2013.01)

(56) References Cited

FOREIGN PATENT DOCUMENTS

| | | |
|---|---|---|
| JP | 3962153 B2 | 8/2007 |
| JP | 2008-17839 A | 1/2008 |
| JP | 2014-513918 A | 6/2014 |
| JP | 2016-146777 A | 8/2016 |
| WO | 2005/037984 A1 | 4/2005 |
| WO | 2012/112572 A2 | 8/2012 |
| WO | 2016/106280 A1 | 6/2016 |
| WO | 2016/106289 A1 | 6/2016 |
| WO | 2016/121994 A1 | 8/2016 |
| WO | 2016/129220 A1 | 8/2016 |

OTHER PUBLICATIONS

Russian Office Action issued in Russian Application No. 2018105093/10(007739), dated Jun. 4, 2018.

Bejder et al., "Experience in the use of fluoropolymer materials in aviation technology", Ros. chem. f. (Zh.M., D.I. Mendeleev Chemical Society of the Russian Federation), vol. 52, No. 3, pp. 1-44, 2008.

Evsyukova, "The influence of technological factors and the structure of modifiers on the hydrophobic properties of fibrous materials and products of light industry", Autoabstract, Moscow, pp. 1-24, 2010.

International Search report from Patent Application No. PCT/JP2016/003319, dated Oct. 18, 2016.

International Preliminary Report on Patentability from Patent Application No. PCT/JP2016/003319, dated Jan. 16, 2018.

Eiji Fujita, "Fuso Jushi no Hyomen Kaimen no Seigyo Gijutsu to sono Oyo", May 13, 2015.

Office Action issued in New Zealand Counterpart Patent Appl. No. 738915, dated May 24, 2018.

\* cited by examiner

CONTAINER FOR CELL ADMINISTRATION, STORAGE OR CULTURING

TECHNICAL FIELD

The present invention relates to a container to be used for administering, storing or culturing mammal cells, wherein the surface of the container in contact with the mammal cells is formed of a fluororesin having one or more —$CF_3$ terminal groups, or a fluororesin having a total number of non-fluorinated group terminals and —$CF_2H$ group terminals in the fluororesin of 70 or less per $1 \times 10^6$ carbon atoms.

BACKGROUND ART

Pluripotent stem cells such as embryonic stem cells (ES cells) and induced pluripotent stem cells (iPS cells) are cells having limitless proliferation abilities and multipotency to diversified tissue cells. Human pluripotent stem cells are expected to be applied to regenerative medicine wherein the human pluripotent stem cells are in vitro differentiation-induced to cells having various types of functions, which are then administered to patients expected to exhibit the administration effect. Further, also somatic stem cells such as mesenchymal stem cells are expected to exhibit the therapeutic effect obtained by release of trophic factors and cytokines, and the effect of homing to damaged sites of tissues and thereafter differentiating to their constituting cells and complementing and restoring the sites, and clinical studies thereof have been attempted. In order to achieve these, it is needed that high-quality cells are stably cultured or stored in large amounts, and administered with their quality being held.

As a container for culturing floating cells, a bag-shape culturing container (bag) is devised (Patent Document 1). Such a bag consists of a polymer alloy in which a polymer mixture of a poly(ethylenebutylene)polystyrene block copolymer with a polypropylene is mixed with an ethylene acrylate copolymer, and has a feature in the point of being excellent in transparency and gas permeability. On the other hand, also bags suitable for culturing adhesive cells are devised (Patent Documents 2, 3). The bag disclosed in Patent Document 2 is the one so improved that cells easily adhere to the bag inner surface by enhancing the hydrophilicity by subjecting the surface to a corona discharge treatment. Further, the bag disclosed in Patent Document 3 consists of a synthetic resin sheet having a predetermined bending rigidity in order for the bag not to easily deform in cultivation, and has a feature in the point of being capable of preventing the peeling and death of cells generated due to deformation of the container when the bag is moved.

Further, bags on the market are known, and there are commercially available, for example, a CultiLife® Spin bag (manufactured by Takara Pac Ltd.) using an ethylene (Et)-vinyl acetate (VA) copolymer (EVA) as its material, a VueLife FEP Bag 32-C (manufactured by American Fluoroseal Corp.) using a tetrafluoroethylene (TFE)-hexafluoropropylene (HFP) copolymer (FEP) being a fluororesin as its material, and a culture bag A-1000NL (manufactured by Nipro Corp.).

Any of these bags, however, are not ones suppressing adhesion of adhesive cells on the bag inner surface and keeping or culturing cells in a floating state.

Meanwhile, it is known that when the surface of food heating and processing appliances is coated with a fluororesin film in which unstable terminal groups of a TFE-perfluoroalkylvinyl ether (PFVE) copolymer (PFA) are fluorinated to eliminate the unstable terminal groups, the stainproofness to scorching is improved (Patent Document 4). However, the cell adhesiveness by the fluororesin whose terminal groups have been fluorinated is not known.

PRIOR ART DOCUMENTS

Patent Documents

Patent Document 1: Japanese unexamined Patent Application Publication No. 03-65177
Patent Document 2: Japanese unexamined Patent Application Publication No. 06-98756
Patent Document 3: Japanese unexamined Patent Application Publication No. 2008-17839
Patent Document 4: Japanese Patent No. 3962153

SUMMARY OF THE INVENTION

Object to be Solved by the Invention

An object of the present invention is to provide a container capable of administering, storing or preparing a mammal cell-containing liquid having a high concentration and a high proportion of living cells.

Means to Solve the Object

As a result of exhaustive studies to solve the problem, the present inventors have found that when mammal cells are administered by using a container which surface in contact with the mammal cells is formed of a fluororesin having one or more —$CF_3$ terminal groups, or a fluororesin having a total number of non-fluorinated group terminals and —$CF_2H$ group terminals in the fluororesin of 70 or less per $1 \times 10^6$ carbon atoms, and mammal cells are stored or cultured in such a container, the cell adhesion to the container inner surface and the cell survival rate reduction are effectively suppressed, and a mammal cell-containing liquid having a high concentration and a high proportion of living cells can be administered, stored or prepared. This finding has led to the completion of the present invention.

That is, the present invention is as follows.

(1) A container for administering, storing or culturing a mammal cell, wherein the surface of the container in contact with the mammal cell is formed of a fluororesin having a total number of a non-fluorinated group terminal and a —$CF_2H$ group terminal in the fluororesin of 70 or less per $1 \times 10^6$ carbon atoms.

(2) A container for administering, storing or culturing a mammal cell, wherein the surface of the container in contact with the mammal cell is formed of a fluororesin having one or more —$CF_3$ terminal groups.

(3) The container for administering, storing or culturing a mammal cell according to the (2), wherein the surface of the container in contact with the mammal cell is formed of a fluororesin having a number of non-fluorinated group terminals of 70 or less per $1 \times 10^6$ carbon atoms.

(4) The container for administering, storing or culturing a mammal cell according to any one of the (1) to (3), wherein the fluororesin is at least one fluororesin selected from a tetrafluoroethylene-hexafluoropropylene-based copolymer and a tetrafluoroethylene-perfluoroalkylvinyl ether-based copolymer.

(5) The container for administering, storing or culturing a mammal cell according to any one of the (1) to (4), wherein the container is a bag.

(6) The container for administering, storing or culturing a mammal cell according to any one of the (1) to (5), wherein the mammal cell is an adhesive cell.
(7) The container for administering, storing or culturing a mammal cell according to any one of the (1) to (6), wherein the mammal cell is a mesenchymal stem cell.

Effect of the Invention

When by using the container for administration, storage or cultivation according to the present invention, a mammal cell-containing liquid is administered or stored, or mammal cells are cultured, since the cell adhesion to the container inner surface and the cell survival rate reduction can effectively be suppressed, there is enabled administration, storage or preparation of the mammal cell-containing liquid having a high concentration and a high proportion of living cells, which contributes to the regenerative medicine using the mammal cell-containing liquid (suspension liquid).

MODE OF CARRYING OUT THE INVENTION

Figure 1:
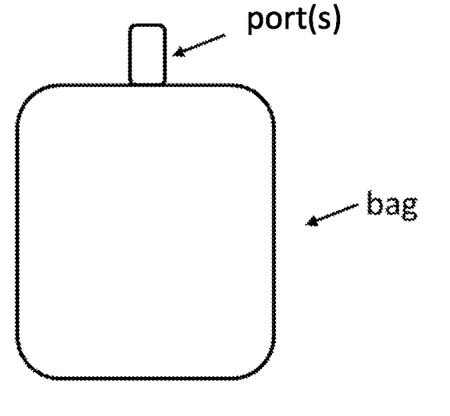
FIG. 1 is a schematic view showing a bag with port(s).

The container for administration, storage or cultivation according to the present invention (hereinafter, referred to simply as "container according to the present invention" in some cases) is not especially limited as long as in the container for administration, storage or cultivation of mammal cells, the surface thereof in contact with the mammal cells (mammal cell-containing liquid) is formed of a fluororesin having one or more —$CF_3$ terminal groups or a fluororesin having a total number of non-fluorinated group terminals and —$CF_2H$ group terminals in the fluororesin of 70 or less per $1\times10^6$ carbon atoms (hereinafter, these fluororesins are generically referred to as "the present fluororesin" in some cases); and the container as a whole is optionally formed of the present fluororesin. The container according to the present invention has a feature in that the container surface in contact with mammal cells is formed of the present fluororesin. When a mammal cell-containing liquid is administered or stored, or mammal cells are cultured by using a container having such a feature, since the cell adhesion and the cell survival rate reduction are effectively suppressed, the container according to the present invention can suitably be used for administration and/or storage of a floating cell-containing liquid and the cultivation of floating cells, and besides, for administration and/or storage of an adhesive cell-containing liquid and floating cultivation of adhesive cells. In the case of the use for administration and/or storage of a cell-containing liquid, and floating cultivation of cells, the container is preferably one in which the container inner surface is not coated with (or disposed on by) a cell-adhesive substance such as Matrigel, entactin, fibronectin, a temperature-responsive polymer (PIPAAm or the like), polycation (polylysine or the like), gelatin, lectin, polysaccharide (hyaluronic acid or the like), polylactic acid, polyglycolic acid, ε-aminocaprolactone, I-type collagen, IV-type collagen, chitosan and laminin. Here, in the present invention, "storage" includes storage during transportation.

The floating cells include ones such as red blood cells, and (peripheral blood-derived) white blood cells (neutrophil leucocytes, mononuclear leucocytes [monocytes and lymphocytes], macrophages, and the like).

Examples of the adhesive cells include: stem cells including pluripotent stem cells such as embryonic stem cells (ES cells), embryonic germ cells (EG cells), germline stem cells (GS cells) and induced pluripotent stem cells (iPS cells); multipotent stem cells such as mesenchymal stem cells, hematopoietic stem cells and nervous stem cells, and unipotent stem cells (precursor cells) such as myocardium precursor cells, vascular endothelium precursor cells, neuronal precursor cells, fat precursor cells, dermal fibroblasts, skeletal muscle myoblasts, osteoblasts and odontoblasts; and mature cells such as myocardium cells, vascular endothelial cells, nerve cells, fat cells, dermal fibrocytes, skeletal myocytes, osteocytes, hepatocytes (liver cells), umbilical cord vein endothelial cells, dermal minute lymphatic endothelial cells, keratinocytes, bronchial epithelial cells, melanocytes, smooth muscle cells and dental cells. Mesenchymal stem cells are preferable.

The present fluororesin is preferably one having no —$CF_2H$ group terminals, and in the fluororesin, the total number of non-fluorinated group terminals (for example, functional groups such as —COF, —COOH, —COOH associated with water, —$CH_2OH$, —$CONH_2$ and —$COOCH_3$) and —$CF_2H$ group terminals is preferably 70 or less per $1\times10^6$ carbon atoms, and more preferably 35 or less per $1\times10^6$ carbon atoms. Further, the number is still more preferably 20 or less per $1\times10^6$ carbon atoms, and especially preferably 10 or less per $1\times10^6$ carbon atoms.

That is, one aspect of the present invention includes a container for administering, storing or culturing mammal cells, wherein the surface of the container in contact with the mammal cells is formed of a fluororesin having a total number of non-fluorinated group terminals and —$CF_2H$ group terminals in the fluororesin of 70 or less per $1\times10^6$ carbon atoms.

The number per $1\times10^6$ carbon atoms of the —COF, —COOH, —COOH associated with water, —$CH_2OH$, —$CONH_2$, —$COOCH_3$ and —$CF_2H$ can be calculated by FT-IR.

Further, the present fluororesin suffices if having one or more —$CF_3$ terminal groups and having a more stabilized terminal structure; and the present fluororesin includes a fluororesin in which a part of non-fluorinated group terminals is fluorinated and which has —$CF_3$.

The —$CF_3$ terminal group can be analyzed by a high-temperature $^{19}F$ NMR measurement.

In the present invention, the "non-fluorinated group terminal" means a terminal having some reactivity and usually called an unstable terminal, and specifically includes functional groups such as —COF, —COOH, —COOH associated with water, —$CH_2OH$, —$CONH_2$ and —$COOCH_3$.

The total number of the non-fluorinated group terminals (for example, functional groups such as —COF, —COOH, —COOH associated with water, —$CH_2OH$, —$CONH_2$ and —$COOCH_3$) in the present fluororesin is preferably 70 or less per $1\times10^6$ carbon atoms, more preferably 50 or less per $1\times10^6$ carbon atoms, still more preferably 35 or less per $1\times10^6$ carbon atoms, further still more preferably 15 or less per $1\times10^6$ carbon atoms, further still more preferably 10 or less per $1\times10^6$ carbon atoms, especially preferably 5 or less per $1\times10^6$ carbon atoms, and further especially preferably 2 or less per $1\times10^6$ carbon atoms.

That is, one aspect of the present invention includes a container for administering, storing or culturing mammal cells, wherein the surface of the container in contact with the mammal cells is formed of a fluororesin having one or more —CF₃ terminal groups in which fluororesin the number of non-fluorinated group terminals is 70 or less per $1 \times 10^6$ carbon atoms.

The present fluororesin specifically includes polytetrafluoroethylene (PTFE), a tetrafluoroethylene (TFE)-hexafluoropropylene (HFP)-based copolymer (FEP) and a TFE-perfluoroalkylvinyl ether (PAVE)-based copolymer (PFA); among these, FEP and PFA can be preferably exemplified and FEP can be suitably exemplified.

The "TFE-HFP-based copolymer" means a copolymer containing at least TFE and HFP. That is, the "TFE-HFP-based copolymer" includes, in addition to a binary copolymer (TFE/HFP copolymer; FEP) of TFE and HFP, also a ternary copolymer such as a copolymer of TFE, HFP and vinyl fluoride (VF) (TFE/HFP/VF copolymer), a copolymer of TFE, HFP and vinylidene fluoride (VDF) (TFE/HFP/VDF copolymer) and a copolymer of TFE, HFP and a perfluoro(alkylvinyl ether)(PAVE) (TFE/HFP/PAVE copolymer), a quaternary copolymer such as a copolymer of TFE, HFP, VF and VDF (TFE/HFP/VF/VDF copolymer), a copolymer of TFE, HFP, VF and PAVE (TFE/HFP/VF/PAVE copolymer) and a copolymer of TFE, HFP, VDF and PAVE (TFE/HFP/VDF/PAVE copolymer), and a quinary copolymer such as a copolymer of TFE, HFP, VF, VDF and PAVE (TFE/HFP/VF/VDF/PAVE copolymer).

The TFE-HFP-based copolymer is preferably a TFE/HFP copolymer or a TFE/HFP/PAVE copolymer. The mass ratio of TFE and HFP in such a TFE/HFP copolymer is preferably 80 to 97/3 to 20, and more preferably 84 to 92/8 to 16. Further, the mass ratio of TFE, HFP and PAVE in the TFE/HFP/PAVE copolymer is preferably 70 to 97/3 to 20/0.1 to 10, and more preferably 81 to 92/5 to 16/0.3 to 5.

The "TFE-PAVE-based copolymer" means a copolymer containing at least TFE and PAVE. That is, the "TFE-PAVE-based copolymer" covers, in addition to a binary copolymer of TFE and PAVE (TFE/PAVE copolymer; PFA), also a ternary copolymer such as a copolymer of TFE, PAVE and hexafluoropropylene (HFP) (TFE/PAVE/HFP copolymer), a copolymer of TFE, PAVE and vinylidene fluoride (VDF) (TFE/PAVE/VDF copolymer) and a copolymer of TFE, PAVE and chlorotrifluoroethylene (CTFE) (TFE/PAVE/CTFE copolymer), a quaternary copolymer such as a copolymer of TFE, PAVE, HFP and VDF (TFE/PAVE/HFP/VDF copolymer), a copolymer of TFE, PAVE, HFP and CTFE (TFE/PAVE/HFP/CTFE copolymer) and a copolymer of TFE, PAVE, VDF and CTFE (TFE/PAVE/VDF/CTFE copolymer), and a quinary copolymer such as a copolymer of TFE, PAVE, HFP, VDF and CTFE (TFE/PAVE/HFP/VDF/CTFE copolymer).

PAVE constituting the PAVE unit is not especially limited, and examples thereof include perfluoro(methyl vinyl ether) [PMVE], perfluoro(ethyl vinyl ether) [PEVE], perfluoro(propyl vinyl ether) [PPVE], perfluoro(butyl vinyl ether), perfluoro(pentyl vinyl ether), perfluoro(hexyl vinyl ether) and perfluoro(heptyl vinyl ether).

The mass ratio of TFE and PAVE in the TFE-PAVE-based copolymer is preferably 90 to 98/2 to 10, and more preferably 92 to 97/3 to 8.

The present fluororesin can be fabricated by subjecting terminal groups of a fluororesin synthesized according to a usual method of suspension polymerization, emulsion polymerization or the like to a fluorination treatment by a known method such as a method in which before a fluororesin is melt extruded, the fluororesin and a fluorine-containing compound (for example, a fluorine radical source) are contacted with each other to carry out a stabilization treatment, and a method in which pellets of a fluororesin obtained after the fluororesin is melt extruded and a fluorine-containing compound are contacted with each other to carry out a fluorination treatment. Further, the present fluororesin can also be obtained by using a chain transfer agent and a polymerization catalyst capable of controlling terminal groups together with a fluorine monomer in production (polymerization reaction) of the fluororesin. Further, as the present fluororesin, commercially available products can be used. The fluorination treatment can also be carried out by contacting a fluorine-containing compound with moldings molded from fluororesins, like films molded by melting fluororesins, containers molded from the films and containers molded from fluororesins. Further, these treatment methods can also be combined.

That is, it is not needed that the total number of the non-fluorinated group terminals and the total number of the non-fluorinated group terminals and —CF₂H group terminals are 70 or less per $1 \times 10^6$ carbon atoms in each stage of fluororesins, pellets and films to become raw materials, and it suffices if on the surface of a final container in contact with cells, the total number thereof is 70 or less per $1 \times 10^6$ carbon atoms. Further, in the case of a fluororesin having one or more —CF₃ terminal groups, it is not needed that the number of the —CF₃ terminal groups is one or more in each stage of fluororesins, pellets and films to become raw materials, and it suffices if on the surface of a final container in contact with cells, the fluororesin has one or more —CF₃ terminal groups.

The fluorine radical source is not especially limited, but examples thereof include a halogen fluoride such as IF₅ and ClF₃, F₂ gas, CoF₃, AgF₂, UF₆, OF₂, N₂F₂ and CF₃OF. The F₂ gas is optionally of a concentration of 100%, but, from the safety aspect, is used by being mixed with an inert gas and thereby diluted to 5 to 50% by mass, preferably 15 to 30% by mass. Examples of the inert gas include nitrogen gas, helium gas and argon gas, and from the viewpoint of the cost efficiency, nitrogen gas is preferable.

The fluorination treatment is carried out at a temperature of preferably 20 to 220° C., and more preferably 100 to 200° C. The fluorination treatment is carried out preferably for 5 to 30 hours, and more preferably for 10 to 20 hours.

The container obtained by the present invention is optionally the one in which the arithmetic mean roughness (Ra) of the surface roughness, the root-mean-square roughness (RMS) of the surface roughness, and the surface free energy have been regulated. Examples of the container include one having its container inner surface having an Ra of the surface roughness of 3.5 to 6.5 nm, an RMS of the surface roughness of 4.5 to 8.0 nm, and a surface free energy of 16.5 to 18.5 (mJ/m²).

Examples of forms of the container according to the present invention include a dish, a well plate, a bag, a bottle, a centrifugal tube, a vial, a syringe and a tube; in the case where the container according to the present invention is a container for administering cells, preferable are a syringe, a bag (for drip), a bottle (for drip), and a tube; in the case where the container according to the present invention is a container for storing cells, preferable are a dish, a well plate, a bag, a bottle, a centrifugal tube and a vial; and in the case where the container according to the present invention is a container for culturing cells, preferable are a dish, a well plate, a bag and a bottle. Particularly the container according to the present invention having a bag shape, since it can be applied to every application for administering, storing and culturing cells, can suitably be exemplified.

The dish, well plate, bag, bottle, centrifugal tube, vial, syringe, tube and the like can be produced by molding methods including compression molding, extrusion, transfer molding, inflation molding, blow molding, injection molding, rotational molding, lining molding, foam extrusion and film molding, as required in combination with sealing means such as heat sealing, high-frequency fusion and ultrasonic fusion.

The bag can be produced specifically by overlapping films (sheets) of the present fluororesin material and heat sealing edge portions by using an impulse sealer.

The film to be used for molding of the bag may be a single-layer film or a laminated film consisting of a multi-layer of two or more layers; and in the case of the laminated film consisting of a multilayer, it suffices if the bag is so molded that at least the inner surface in contact with mammal cells is a layer film of the present fluororesin material, and the other layer films are each allowed to be even a layer film of a material (for example, a polyolefinic resin material) different from the present fluororesin. The lamination of the films is carried out by using a method such as a heat lamination method, a heat compression method, a high-frequency heating method, a solvent casting method and an extrusion lamination method.

Further, the container according to the present invention can also be obtained by subjecting a base material, such as a dish, a well plate, a bag, a bottle, a centrifugal tube, a vial, a syringe and a tube, produced of a glass, a metal, a resin or the like, to a coating treatment with a coating agent consisting of the present fluororesin. Any methods can be employed according to the form of the base material. Examples of such a coating treatment include spin coating, spray coating, bar coating, roll coating, dipping, brush coating, rotolining and electrostatic coating. The base material is coated with the fluororesin coating agent, and thereafter subjected to a drying treatment and a high-temperature heating treatment to thereby form a coating layer. Further, the coating layer is allowed to be made to be thick to any thickness by further double-coating a coating agent containing the present fluororesin.

The container according to the present invention can be used, for example, for the case where a mammal cell-containing liquid is cryopreserved, the case where a mammal cell-containing liquid is stored (at least for 6 hours) at a temperature at which the liquid is not frozen (usually in the range of 0 to 37° C., preferably 0 to 25° C. [room temperature]), the case where floating or adhesive mammal cells are produced in a large amount by a suspension cultivation method, or the case where the mammal cell-containing liquid after storage at a temperature at which the liquid is not frozen is administered (transplanted) as it is without being transferred to another container.

Hereinafter, the present invention will be described more specifically by way of Examples, but the technical scope of the present invention is not limited to these Examples.

Example 1

1. Production of Cell Bags

Three kinds of films of 16 cm×15 cm in size and 100 μm in thickness were heat sealed by using an impulse sealer under the conditions of a sealing time of 50 sec, a sealing pressure of 0.2 MPa and a sealing width of 5 mm to thereby produce 12 kinds of cell bags (cell bags A to C [Comparative Example Samples 1 to 3], cell bags D to G [Example Samples 1 to 4], a cell bag H (Comparative Example Sample 4), cell bags I to K [Example Samples 5 to 7], and a cell bag L [Comparative Example Sample 5])(see Table 2). Here, a cell bag M (Comparative Example Sample 6) used was a polyvinyl chloride-made cell bag (obtained by processing a Kawasumi quadruple bag ACP-AMP, manufactured by Kawasumi Laboratories, Inc.) (see Table 2).

1-1 Measurement of the Number of Non-Fluorinated Group Terminals and the Number of —$CF_2H$ Group Terminals Samples of corresponding resins of about 250 to 300 μm in thickness were fabricated, and analyzed by using an FT-IR Spectrometer 1760X (manufactured by PerkinElmer, Inc.).

The samples of corresponding resins of about 250 to 300 μm in thickness were fabricated by rolling pellets by a hydraulic press. Further, the measurement was carried out by using the films (fabricated from the pellets by melt molding) constituting the cell bags as they were, and in the case where the thickness was insufficient, by overlapping the films.

Difference spectra from standard samples (samples fluorinated enough until substantially no difference is any more observed in spectra) were acquired; absorbances of each peak were read; and the number of non-fluorinated group terminals and the number of —$CF_2H$ group terminals per $1\times10^6$ carbon atoms were calculated for each sample according to the following equation. The number of non-fluorinated group terminals and the number of —$CF_2H$ group terminals in each of the cell bags A to M are shown in Table 2.

The numbers of non-fluorinated group terminals and —$CF_2H$ group terminals (per $1\times10^6$ carbon atoms)=l·k/t l: absorbance k: correction factor (see Table 1)

t: sample thickness (mm)

TABLE 1

Absorption Wave Number and Correction Factor of each Non-Fluorinated Group Terminal Group and —$CF_2H$ Group Terminal

| Terminal Group | Absorption Wave Number (cm$^{-1}$) | Correction Factor |
|---|---|---|
| COF | 1884 | 405 |
| COOH (free) | 1813 | 455 |
| COOH (bonded) | 1775 1790 | 455 |
| COOCH$_3$ | 1795 | 355 |
| CONH$_2$ | 3438 | 480 |
| CH$_2$OH | 3648 | 2325 |
| CF$_2$H | 3006 | 26485 |

TABLE 2

The Number of Non-Fluorinated Group Terminals and the Number of —$CF_2H$ Group Terminals of Cell Bag

| | Cell Bag | Fluoro-resin | Before Cell Bag Production | | After Cell Bag Production | |
|---|---|---|---|---|---|---|
| | | | The Number of Non-Fluorinated Group Terminals | The Number of —$CF_2H$ Group Terminals | The Number of Non-Fluorinated Group Terminals | The Number of —$CF_2H$ Group Terminals |
| Comparative Example Sample 1 | A | FEP | 0 | 486 | 15 | 507 |

TABLE 2-continued

The Number of Non-Fluorinated Group Terminals and the Number of —CF$_2$H Group Terminals of Cell Bag

| | Cell Bag | Fluoro-resin | Before Cell Bag Production | | After Cell Bag Production | |
|---|---|---|---|---|---|---|
| | | | The Number of Non-Fluorinated Group Terminals | The Number of —CF$_2$H Group Terminals | The Number of Non-Fluorinated Group Terminals | The Number of —CF$_2$H Group Terminals |
| Comparative Example Sample 2 | B | FEP | 19 | 392 | 21 | 424 |
| Comparative Example Sample 3 | C | FEP | 30 | 230 | 43 | 256 |
| Example Sample 1 | D | FEP | 46 | 0 | 68 | 0 |
| Example Sample 2 | E | FEP | 0 | 0 | 13 | 0 |
| Example Sample 3 | F | FEP | 2 | 0 | 12 | 0 |
| Example Sample 4 | G | FEP | 0 | 0 | 7 | 0 |
| Comparative Example Sample 4 | H | PFA | 178 | 138 | 201 | 159 |
| Example Sample 5 | I | PFA | 0 | 0 | 25 | 0 |
| Example Sample 6 | J | PFA | 0 | 0 | 11 | 0 |
| Example Sample 7 | K | PFA | 0 | 0 | 29 | 0 |
| Comparative Example Sample 5 | L | — (polyethylene) | — | — | — | — |
| Comparative Example Sample 6 | M | — (polyvinyl chloride) | — | — | — | — |

"Before Cell Bag Production" in the table means that the samples were obtained by rolling fluororesin pellets used for cell bag production.
"After Cell Bag Production" in the table means that the samples were obtained from films (fabricated by melt molding from the pellets) constituting the cell bags.

1-2 Measurement of Presence/Absence of a —CF$_3$ Terminal Group

The corresponding resin films were melted at 370° C. and fabricated into strands; and spectra thereof by a high-temperature $^{19}$F NMR were measured by using a nuclear magnetic resonance spectrometer AVANCE 300WB (manufactured by Bruker Corp.).

Difference spectra from strands fabricated by melting resins which had the same compositional ratios as the corresponding resins and in which no —CF$_3$ terminal groups were present were acquired; when a peak was observed at δ=–82 ppm, —CF$_3$ terminal groups were judged to be present, and when no peak was observed at δ=–82 ppm, —CF$_3$ terminal groups were judged to be absent. The presence/absence of the —CF$_3$ terminal groups in each of the cell bags A to M are shown in Table 3.

TABLE 3

Presence/Absence of —CF$_3$ Terminal Group

| | Cell Bag | Fluororesin | —CF$_3$ Terminal |
|---|---|---|---|
| Comparative Example Sample 1 | A | FEP | absent |
| Comparative Example Sample 2 | B | FEP | absent |
| Comparative Example Sample 3 | C | FEP | absent |
| Example Sample 1 | D | FEP | present |
| Example Sample 2 | E | FEP | present |
| Example Sample 3 | F | FEP | present |
| Example Sample 4 | G | FEP | present |
| Comparative Example Sample 4 | H | PFA | absent |
| Example Sample 5 | I | PFA | present |
| Example Sample 6 | J | PFA | present |
| Example Sample 7 | K | PFA | present |
| Comparative Example Sample 5 | L | - (polyethylene) | — |
| Comparative Example Sample 6 | M | - (polyvinyl chloride) | — |

Example 2

2. Storage of Human Bone Marrow-Derived Mesenchymal Stem Cells (hMSCs) by Using the Cell Bag In the case where cells were stored by using the cell bag of Example 1, it was analyzed whether the cell adhesion could be suppressed to thereby store the cells in a floating state.

2-1 Method 2-1-1 Preparation of a Cell Storing Liquid

A 6.0 (w/v) % trehalose-containing Lactec® injection (manufactured by Otsuka Pharmaceutical Factory, Inc.) and a low-molecular dextran L injection (10 (w/v) % dextran-containing Lactec injection) (manufactured by Otsuka Pharmaceutical Factory, Inc.) were mixed in a ratio of 1:1 to thereby prepare a cell storing liquid.

2-1-2 Preparation of Mammal Cells

[1] $4 \times 10^5$ hMSCs (manufactured by Lonza Ltd., PT-2501) were cultured in the presence of an MSC culture medium (manufactured by Lonza Ltd., PT-3001) in a 75-cm² flask in an incubator at 37° C. in 5% $CO_2$, and subcultured in an about 90% confluent by a usual method.

[2] The culture medium for the subcultured hMSCs (cells subcultured three times, nearly 100% confluent) was removed by an aspirator; and the hMSCs were rinsed with PBS (manufactured by Invitrogen Corp.) of 8 mL per flask.

[3] The PBS was removed by an aspirator; and a trypsin-EDTA (manufactured by Lonza Ltd., CC-3232) of 3.75 mL per flask was added to the resultant and allowed to stand still at room temperature for 5 min.

[4] The resultant was slowly shaken until about 90% of the hMSCs was peeled under observation with a microscope.

[5] An MSC culture medium of 3.75 mL per flask was added to stop the trypsin reaction; and the hMSCs were recovered by pipetting, and transferred to a 50-mL centrifugal tube.

[6] The resultant was subjected to a centrifugation at 600×g for 5 min at 25° C.

[7] The supernatant was removed by an aspirator; and the cell storing liquid of 3 mL per flask was added and hMSC pellets (precipitates) were suspended.

[8] 10 μL of the hMSC-BM suspension liquid was collected; the number of cells was measured by using a cell-counting plate; and the cell storing liquid was added so that the number of cells became $5 \times 10^5$ cells/mL, and the resultant was cooled with ice.

2-1-3 Storage of the Mammal Cells

[1] 3 mL of the hMSC-containing cell storing liquid of $5 \times 10^5$ cells/mL was seeded in each of 13 kinds of the cell bags A to M each.

[2] After the cell suspension liquid was allowed to stand still and stored for 6 hours in an incubator (25° C., 5% $CO_2$) (manufactured by As One Co., Ltd., PIC100), a part thereof (20 μL) was recovered, and mixed with 20 μL of a 0.4% trypan blue (manufactured by Gibco); the cell concentration and the number of living cells of the cell suspension liquid were measured under a microscope (ECLIPSE TS100, manufactured by Nikon Corp.) by using a cell-counting plate; and the respective cell recovery rates (see Tables 4, 7 and 10) and cell survival rates (see Tables 5, 8 and 11) were calculated. Further, a part of the bag was cut out by scissors and put on a 6-well plate; and cells adhering on the bag were observed under a microscope (IX-70, manufactured by Olympus Corp.). Here, the results in Table 4 to Table 6, Table 7 to Table 9 and Table 10 to Table 12 were each obtained by an independent experiment (having a different preparation time for hMSCs).

TABLE 4

Cell Recovery Rate (%) 1 of hMSCs

| | Cell Bag | Immediately After Storage Initiation | After 6-Hour Storage |
|---|---|---|---|
| | - (Pre) | 100 ± 3 | |
| Comparative Example Sample 1 | A | | 39 ± 1 |
| Comparative Example Sample 2 | B | | 43 (n = 1) |
| Comparative Example Sample 3 | C | | 34 ± 13 |
| Example Sample 1 | D | | 50 ± 2 |

TABLE 4-continued

Cell Recovery Rate (%) 1 of hMSCs

| | Cell Bag | Immediately After Storage Initiation | After 6-Hour Storage |
|---|---|---|---|
| Example Sample 3 | F | | 69 ± 4** |
| Example Sample 4 | G | | 99 (n = 1) |
| Comparative Example Sample 4 | H | | 40 ± 12 |
| Example Sample 6 | J | | 70 ± 14** |
| Example Sample 7 | K | | 80 ± 8*** |
| Comparative Example Sample 5 | L | | 38 ± 12 |
| Comparative Example Sample 6 | M | | 36 ± 4 |

The cell recovery rate (%) is indicated as the proportion of the total number of cells in the cell suspension liquid after storage to the total number of cells in the suspension liquid immediately after storage initiation (Pre) ([the total number of cells in the cell suspension liquid after storage/the total number of cells in the suspension liquid immediately after storage initiation (Pre) × 100]) (average value ± standard deviation, n = 3). Here, in the table, "" and "*" indicate that there is a statistically significant difference (p < 0.01 and p < 0.001, respectively) from the cell bag L (Comparative Example Sample 5) by Dunnett's method.

TABLE 5

Cell Survival Rate (%) 1 of hMSCs

| | Cell Bag | Immediately After Storage Initiation | After 6-Hour Storage |
|---|---|---|---|
| | - (Pre) | 97 ± 2 | |
| Comparative Example Sample 1 | A | | 89 ± 6 |
| Comparative Example Sample 2 | B | | 87 (n = 1) |
| Comparative Example Sample 3 | C | | 93 ± 3 |
| Example Sample 1 | D | | 93 ± 3 |
| Example Sample 3 | F | | 96 ± 0* |
| Example Sample 4 | G | | 93 (n = 1) |
| Comparative Example Sample 4 | H | | 93 ± 1 |
| Example Sample 6 | J | | 95 ± 1* |
| Example Sample 7 | K | | 96 ± 1* |
| Comparative Example Sample 5 | L | | 81 ± 14 |
| Comparative Example Sample 6 | M | | 90 ± 7 |

The cell survival rate (%) is indicated as the proportion of the number of living cells to the total number of cells in the cell suspension liquid ([the number of living cells in the cell suspension liquid/the total number of cells in the cell suspension liquid × 100]) (average value ± standard deviation, n = 3). Here, in the table, "*" indicates that there is a statistically significant difference (p < 0.05) from the cell bag L (Comparative Example Sample 5) by Dunnett's method.

TABLE 6

Recovery Rate 1 of Living Cells of hMSCs

| | Cell Bag | Immediately After Storage Initiation | After 6-Hour Storage |
|---|---|---|---|
| | - (Pre) | 97 ± 4 | |
| Comparative Example Sample 1 | A | | 34 ± 2 |
| Comparative Example Sample 2 | B | | 37 (n = 1) |
| Comparative Example Sample 3 | C | | 31 ± 12 |
| Example Sample 1 | D | | 46 ± 1 |
| Example Sample 3 | F | | 66 ± 4** |
| Example Sample 4 | G | | 92 (n = 1) |
| Comparative Example Sample 4 | H | | 37 ± 11 |
| Example Sample 6 | J | | 66 ± 13** |

TABLE 6-continued

Recovery Rate 1 of Living Cells of hMSCs

| | Cell Bag | Immediately After Storage Initiation | After 6-Hour Storage |
|---|---|---|---|
| Example Sample 7 | K | | 77 ± 8*** |
| Comparative Example Sample 5 | L | | 31 ± 13 |
| Comparative Example Sample 6 | M | | 32 ± 4 |

The recovery rate of living cells is indicated as a value of the cell recovery rate value multiplied by the cell survival rate value (average value ± standard deviation, n = 3). Here, in the table, "" and "*" indicate that there is a statistically significant difference (p < 0.01 and p < 0.001, respectively) from the cell bag L (Comparative Example Sample 5) by Dunnett's method.

2-2 Results

The recovery rates of the hMSCs after storage were, as shown in Table 4, in the case of using the cell bags A, B, C, H, L and M (Comparative Example Samples 1, 2, 3, 4, 5 and 6), 39%, 43%, 34%, 40%, 38% and 36%, respectively, and by contrast, in the case of using the cell bags D, F, G, J and K (Example Samples 1, 3, 4, 6 and 7), as high as 50%, 69%, 99%, 70% and 80%, respectively.

Further, the survival rates of the hMSCs after storage were, as shown in Table 5, in the case of using the cell bags D, F, G, J and K (Example Samples 1, 3, 4, 6 and 7), 93%, 96%, 93%, 95% and 96%, respectively, and any one of the rates was as high as 90% or higher.

Consequently, the recovery rates (cell survival rate×cell recovery rate) of the hMSCs surviving after storage were, as shown in Table 6, higher in the case (46%, 66%, 92%, 66% and 77%, respectively) of storage in the cell bags D, F, G, J and K (Example Samples 1, 3, 4, 6 and 7) than in the case (34%, 37%, 31%, 37%, 31% and 32%, respectively) of storage in cell bags A, B, C, H, L and M (Comparative Example Samples 1, 2, 3, 4, 5 and 6).

TABLE 7

Cell Recovery Rate (%) 2 of hMSCs

| | Cell Bag | Immediately After Storage Initiation | After 6-Hour Storage |
|---|---|---|---|
| | - (Pre) | 100 ± 4 | |
| Comparative Example Sample 2 | B | | 30 ± 25 |
| Example Sample 4 | G | | 80 ± 9*** |
| Comparative Example Sample 5 | L | | 25 ± 6 |

The cell recovery rate (%) is indicated as the proportion of the total number of cells in the cell suspension liquid after storage to the total number of cells in the cell suspension liquid immediately after storage initiation (Pre) ([the total number of cells in the cell suspension liquid after storage/the total number of cells in the cell suspension liquid immediately after storage initiation (Pre) × 100]) (average value ± standard deviation, n = 3). Here, in the table, "***" indicates that there is a statistically significant difference (p < 0.001) from the cell bag L (Comparative Example Sample 5) by Dunnett's method.

TABLE 8

Cell Survival Rate (%) 2 of hMSCs

| | Cell Bag | Immediately After Storage Initiation | After 6-Hour Storage |
|---|---|---|---|
| | - (Pre) | 98 ± 1 | |
| Comparative Example Sample 2 | B | | 88 ± 6 |

TABLE 8-continued

Cell Survival Rate (%) 2 of hMSCs

| | Cell Bag | Immediately After Storage Initiation | After 6-Hour Storage |
|---|---|---|---|
| Example Sample 4 | G | | 95 ± 4 |
| Comparative Example Sample 5 | L | | 86 ± 7 |

The cell survival rate (%) is indicated as the proportion of the number of living cells to the total number of cells in the cell suspension liquid ([the number of living cells in the cell suspension liquid/the total number of cells in the cell suspension liquid × 100]) (average value ± standard deviation, n = 3).

TABLE 9

Recovery Rate 2 of Living Cells of hMSCs

| | Cell Bag | Immediately After Storage Initiation | After 6-Hour Storage |
|---|---|---|---|
| | - (Pre) | 98 ± 4 | |
| Comparative Example Sample 2 | B | | 27 ± 24 |
| Example Sample 4 | G | | 76 ± 11*** |
| Comparative Example Sample 5 | L | | 22 ± 7 |

The recovery rate of living cells is indicated as a value of the cell recovery rate value multiplied by the cell survival rate value (average value ± standard deviation, n = 3). Here, in the table, "***" indicates that there is a statistically significant difference (p < 0.001) from the cell bag L (Comparative Example Sample 5) by Dunnett's method.

2-3 Results

The recovery rates of the hMSCs after storage were, as shown in Table 7, in the case of using the cell bags B and L (Comparative Example Samples 2 and 5), 30% and 25%, respectively, and by contrast, in the case of using the cell bag G (Example Sample 4), as high as 80%.

Further, the survival rates of the hMSCs after storage were, as shown in Table 8, in the case of using the cell bag G (Example Sample 4), as high as 95%.

Consequently, the recovery rates (cell survival rate×cell recovery rate) of the hMSCs surviving after storage were, as shown in Table 9, higher in the case (76%) of storage in the cell bag G (Example Sample 4) than in the case (27% and 22%, respectively) of storage in the cell bags B and L (Comparative Example Samples 2 and 5).

TABLE 10

Cell Recovery Rate (%) 3 of hMSCs

| | Cell Bag | Immediately After Storage Initiation | After 6-Hour Storage |
|---|---|---|---|
| | - (Pre) | 100 ± 10 | |
| Comparative Example Sample 2 | B | | 49 ± 9 |
| Example Sample 2 | E | | 83 ± 10* |
| Example Sample 3 | F | | 75 ± 11 |
| Example Sample 5 | I | | 84 ± 9* |
| Example Sample 7 | K | | 67 ± 4 |

The cell recovery rate (%) is indicated as the proportion of the total number of cells in the cell suspension liquid after storage to the total number of cells in the cell suspension liquid immediately after storage initiation (Pre) ([the total number of cells in the cell suspension liquid after storage/the total number of cells in the cell suspension liquid immediately after storage initiation (Pre) × 100]) (average value ± standard deviation, n = 3). Here, in the table, "*" indicates that there is a statistically significant difference (p < 0.05) from the cell bag B (Comparative Example Sample 2) by Dunnett's method.

TABLE 11

Cell Survival Rate (%) 3 of hMSCs

|  | Cell Bag | Immediately After Storage Initiation | After 6-Hour Storage |
|---|---|---|---|
|  | - (Pre) | 97 ± 1 |  |
| Comparative Example Sample 2 | B |  | 92 ± 3 |
| Example Sample 2 | E |  | 93 ± 2 |
| Example Sample 3 | F |  | 93 ± 1 |
| Example Sample 5 | I |  | 91 ± 2 |
| Example Sample 7 | K |  | 92 ± 1 |

The cell survival rate (%) is indicated as the proportion of the number of living cells to the total number of cells in the cell suspension liquid ([the number of living cells in the cell suspension liquid/the total number of cells in the cell suspension liquid × 100]) (average value ± standard deviation, n = 3).

TABLE 12

Recovery Rate 3 of Living Cells of hMSCs

|  | Cell Bag | Immediately After Storage Initiation | After 6-Hour Storage |
|---|---|---|---|
|  | - (Pre) | 97 ± 9 |  |
| Comparative Example Sample 2 | B |  | 45 ± 10 |
| Example Sample 2 | E |  | 77 ± 9* |
| Example Sample 3 | F |  | 69 ± 11 |
| Example Sample 5 | I |  | 76 ± 7 |
| Example Sample 7 | K |  | 61 ± 5 |

The recovery rate of living cells is indicated as a value of the cell recovery rate value multiplied by the cell survival rate value (average value ± standard deviation, n = 3). Here, in the table, "*" indicates that there is a statistically significant difference ($p < 0.05$) from the cell bag B (Comparative Example Sample 2) by Dunnett's method.

2-4 Results

The recovery rates of the hMSCs after storage were, as shown in Table 10, in the case of using the cell bag B (Comparative Example Sample 2), 49%, and by contrast, in the case of using the cell bags E, F, I and K (Example Samples 2, 3, 5 and 7), as high as 83%, 75%, 84% and 67%, respectively.

Further, the survival rates of the hMSCs after storage were, as shown in Table 11, in the case of using the cell bags E, F, I and K (Example Samples 2, 3, 5 and 7), 93%, 93%, 91% and 92%, respectively, and any one of the rates was as high as 90% or higher.

Consequently, the recovery rates (cell survival rate×cell recovery rate) of the hMSCs surviving after storage were, as shown in Table 12, higher in the case (77%, 69%, 76% and 61%, respectively) of storage in the cell bags E, F, I and K (Example Samples 2, 3, 5 and 7) than in the case (45%) of storage in the cell bag B (Comparative Example Sample 2).

Further, the hMSCs after storage were adhered on the inner surface of the cell bags A to C, H, L and M (Comparative Example Samples 1 to 3, 4, 5 and 6), and by contrast, were suppressed in the adhesiveness on the inner surface of the cell bags D to G and I to K (Example Samples 1 to 4 and 5 to 7); and almost no hMSCs were adhered particularly on the inner surface of the cell bags E to G and I to K (Example Samples 2 to 4 and 5 to 7).

These results indicate that the adhesiveness of living cells was significantly suppressed more in the storage of the cells in the cell bags D to G and I to K (Example Samples 1 to 4 and 5 to 7) than in the storage of the cells in the cell bags A to C, H, L and M (Comparative Example Samples 1 to 3, 4, 5 and 6).

Example 3

3. Cultivation of 10T1/2 Cells Derived from Mouse Mesenchymal Stem Cells by Using the Cell Bag In the case where the cells were cultured by using the cell bags produced in Example 1, it was analyzed whether the cell adhesion could be suppressed to thereby culture the cells in a floating state.

3-1 Method

[1] 10T1/2 cells derived from mouse mesenchymal stem cells were suspended in a DMEM (manufactured by Nacalai Tesque, Inc., 08458-45) culture medium containing a 10% FBS (manufactured by Life Technologies Corp., Gibco standard) so that the cell concentration became $1.0 \times 10^5$ cells/mL; 3 mL of the suspension liquid was seeded in two kinds of the cell bag B (Comparative Example Sample 2) and the cell bag G (Example Sample 4) each.

[2] The resultants were cultured in an incubator (37° C., 5% $CO_2$); a part (10 μL) of the cell suspension liquids each was recovered after 4 hours, and 1, 2, 3 and 6 days, and mixed with 10 μL of a 0.4% trypan blue (manufactured by Gibco); and the number of living cells were measured by using a cell-counting plate and the cell survival rates were calculated. Further, cells adhered on the cell bags were observed under an optical microscope (manufactured by Nikon Corp.).

3-2 Results

The survival rates of the 10T1/2 cells after the cultivation were as high as 70% or higher both in the case of using the cell bag G (Example Sample 4) and the cell bag B (Comparative Example Sample 2). By contrast, the proportion of the 10T1/2 cells adhered on the bag inner surface after the cultivation was lower in the case of using the cell bag G than in the case of using the cell bag B.

This result indicates that the adhesiveness of living cells could be significantly suppressed more in the cultivation of the cells in the cell bag G (Example Sample 4) than in the cultivation of the cells in the cell bag B (Comparative Example Sample 2).

The results of Examples 1 to 3 indicate that since when cells are administered, stored or cultured by using the cell bags D to G and I to K (Example Samples 1 to 7), the cell adhesion to the container inner surface and the cell survival rate reduction can effectively be suppressed, a cell-containing liquid having a high concentration and a high proportion of living cells can be administered, stored or prepared.

INDUSTRIAL APPLICABILITY

According to the present invention, a cell-containing liquid having a high concentration and a high proportion of living cells can be administered, stored or prepared, which contributes to regenerative medicine using a mammal cell-containing liquid (suspension liquid).

The invention claimed is:

1. A container for administering, storing or culturing a mammal cell, wherein a surface of the container in contact with the mammal cell is formed of a fluororesin having a total number of a non-fluorinated group terminal and a —$CF_2H$ group terminal in the fluororesin of 70 or less per $1 \times 10^6$ carbon atoms, wherein the fluororesin is at least one fluororesin selected from a tetrafluoroethylene-hexafluoropropylene-based copolymer and a tetrafluoroethylene-perfluoroalkylvinyl ether-based copolymer.

2. The container for administering, storing or culturing a mammal cell according to claim 1, wherein the container is a bag.

3. The container for administering, storing or culturing a mammal cell according to claim 1, wherein the mammal cell is an adhesive cell.

4. The container for administering, storing or culturing a mammal cell according to claim 1, wherein the mammal cell is a mesenchymal stem cell.

5. A container for administering, storing or culturing a mammal cell, wherein a surface of the container in contact with the mammal cell is formed of a fluororesin having one or more —$CF_3$ terminal groups, wherein the fluororesin is at least one fluororesin selected from a tetrafluoroethylene-hexafluoropropylene-based copolymer and a tetrafluoroethylene-perfluoroalkylvinyl ether-based copolymer, wherein a surface of the container in contact with the mammal cell is formed of a fluororesin having a number of the non-fluorinated group terminals of 70 or less per $1\times10^6$ carbon atoms.

6. The container for administering, storing or culturing a mammal cell according to claim 5, wherein the container is a bag.

7. A method for administering, storing, or culturing a mammal cell comprising:
   a step of administering the mammal cell using a container wherein a surface of the container in contact with the mammal cell is formed of a fluororesin having a total number of a non-fluorinated group terminal and a —$CF_2H$ group terminal in the fluororesin of 70 or less per $1\times10^6$ carbon atoms, wherein the fluororesin is at least one fluororesin selected from a tetrafluoroethylene-hexafluoropropylene-based copolymer and a tetrafluoroethylene-perfluoroalkylvinyl ether-based copolymer; or
   a step of storing or culturing the mammal cell within the container.

8. The method for administering, storing, or culturing a mammal cell according to claim 7, wherein the container is a bag.

9. The method for administering, storing, or culturing a mammal cell according to claim 7, wherein the mammal cell is an adhesive cell.

10. The method for administering, storing, or culturing a mammal cell according to claim 9, wherein the mammal cell is a mesenchymal stem cell.

11. A method for administering, storing, or culturing a mammal cell comprising:
    a step of administering the mammal cell using a container wherein a surface of the container in contact with the mammal cell is formed of a fluororesin having one or more —$CF_3$ terminal groups, wherein the fluororesin is at least one fluororesin selected from a tetrafluoroethylene-hexafluoropropylene-based copolymer and a tetrafluoroethylene-perfluoroalkylvinyl ether-based copolymer; or
    a step of storing or culturing the mammal cell within the container,
    wherein a surface of the container in contact with the mammal cell is formed of a fluororesin having a number of the non-fluorinated group terminals of 70 or less per $1\times10^6$ carbon atoms.

12. The method for administering, storing, or culturing a mammal cell according to claim 11, wherein the container is a bag.

* * * * *